(12) United States Patent
Arango

(10) Patent No.: US 10,194,941 B2
(45) Date of Patent: Feb. 5, 2019

(54) CALLUS REMOVAL APPARATUS

(71) Applicant: Alejandro Arango, Deland, FL (US)

(72) Inventor: Alejandro Arango, Deland, FL (US)

( * ) Notice: Subject to any disclaimer, the term of this patent is extended or adjusted under 35 U.S.C. 154(b) by 506 days.

(21) Appl. No.: 15/099,013

(22) Filed: Apr. 14, 2016

(65) Prior Publication Data

US 2017/0296232 A1    Oct. 19, 2017

(51) Int. Cl.
*A45D 29/04* (2006.01)
*A61B 17/54* (2006.01)
*A61B 17/00* (2006.01)
*A61B 17/32* (2006.01)

(52) U.S. Cl.
CPC .............. *A61B 17/54* (2013.01); *A45D 29/04* (2013.01); *A61B 2017/00747* (2013.01); *A61B 2017/320004* (2013.01); *A61B 2017/320008* (2013.01)

(58) Field of Classification Search
CPC .......... A61B 17/54; A61B 2017/00752; A61B 2017/00747; A61B 2017/00761; A61B 2017/32008; A45D 29/04; B27G 17/04
USPC .... 132/75.3, 75.4, 75.5, 75.6, 76.4; D28/59; D24/146, 147, 149; D7/678; 30/26; 451/461; 241/273.1, 273.2, 273.4; 606/131, 133
See application file for complete search history.

(56) References Cited

U.S. PATENT DOCUMENTS

| | | | |
|---|---|---|---|
| D49,710 S * | 9/1916 | Lupo | D28/59 |
| 1,498,156 A | 6/1924 | Drew | |
| 1,620,825 A * | 3/1927 | Mills | B29C 73/26 81/15.2 |
| 2,231,453 A * | 2/1941 | Pitar | A45D 26/0004 451/524 |
| 2,746,461 A | 5/1956 | Bocchino | |
| D186,752 S * | 11/1959 | Dean | 30/26 |
| 4,037,793 A * | 7/1977 | Puustinen | A47J 43/25 241/168 |

(Continued)

FOREIGN PATENT DOCUMENTS

EP    0381962 B1    6/1994

OTHER PUBLICATIONS

AMOS Foot Rasp Callus File Dry Hard Dead Skin Corn Remover, https://www.amazon.co.uk/AMOS-Callous-Exfoliating-Pedicure-Smoother/dp/B00EDJSB14 pages 1-6, Aug. 27, 2015 (see comments on p. 6 for date).*

*Primary Examiner* — Tatiana Nobrega
(74) *Attorney, Agent, or Firm* — Glenn E. Gold, P.A.; Glenn E. Gold

(57) ABSTRACT

A callus removal apparatus includes a hollow main body having opposite first and second end portions and an elongated configuration for ease of gripping by one hand, a callus scraping device fitted on the main body first end portion, and a callus sanding device fitted on and detachable from the main body second end portion. The callus scraping device has a head and an array of spaced apart annular edges exposed at an exterior face of the head and forming apertures extending through the head. The exposed annular edges are capable of removing pieces of a callus by moving the head across and in contact with the callus. The callus sanding device has a panel and a plurality of sanding particles attached on the panel and exposed at the exterior thereof and thus capable of removing pieces of a callus moving the panel across and in contact with the callus.

13 Claims, 8 Drawing Sheets

(56) References Cited

U.S. PATENT DOCUMENTS

| | | | |
|---|---|---|---|
| 4,211,246 A * | 7/1980 | Hokama | A45D 29/12 |
| | | | 132/76.4 |
| D276,276 S * | 11/1984 | Bankier | D24/147 |
| 4,541,443 A | 9/1985 | Brothers et al. | |
| 4,643,207 A | 2/1987 | Grahame | |
| 4,807,360 A * | 2/1989 | Cerier | B26B 21/20 |
| | | | 30/346.5 |
| D412,764 S * | 8/1999 | Godbout | D28/59 |
| 6,142,156 A | 11/2000 | Brunderman | |
| 6,470,895 B1 * | 10/2002 | Miller | A61B 17/54 |
| | | | 132/75.6 |
| 6,514,132 B2 | 2/2003 | Park | |
| 7,093,603 B2 | 8/2006 | Han | |
| 7,267,125 B2 | 9/2007 | Nevakshonoff | |
| 7,347,211 B1 | 3/2008 | Macklin | |
| D596,353 S * | 7/2009 | Yang | D24/147 |
| D596,802 S * | 7/2009 | Yang | D24/147 |
| 7,578,300 B2 | 8/2009 | Ryder | |
| D605,001 S * | 12/2009 | Eide | D7/678 |
| D623,801 S * | 9/2010 | Curran | D24/147 |
| D631,199 S * | 1/2011 | Helm | D28/59 |
| D643,153 S * | 8/2011 | Howlett | D24/147 |
| 8,066,013 B2 | 11/2011 | Tes et al. | |
| D739,981 S * | 9/2015 | Lee | D28/59 |
| D740,490 S * | 10/2015 | Roberts | D28/59 |
| D741,017 S * | 10/2015 | Exley | D28/59 |
| 2004/0167481 A1 | 8/2004 | Carlucci et al. | |
| 2004/0254587 A1 | 12/2004 | Park | |
| 2005/0061343 A1 | 3/2005 | Ebner | |
| 2007/0240730 A1 * | 10/2007 | Ortiz | A45D 29/16 |
| | | | 132/74.5 |
| 2008/0091216 A1 * | 4/2008 | Grace | A61B 17/54 |
| | | | 606/131 |
| 2008/0295855 A1 | 12/2008 | Nguyen et al. | |
| 2009/0004953 A1 | 1/2009 | Kinsey | |
| 2009/0198159 A1 * | 8/2009 | Linzell | A61H 7/003 |
| | | | 601/138 |
| 2010/0037906 A1 * | 2/2010 | Ionis | A61B 17/54 |
| | | | 132/76.5 |
| 2010/0217357 A1 * | 8/2010 | Da Silva | A61B 17/54 |
| | | | 607/88 |
| 2012/0179170 A1 * | 7/2012 | Payne | A45D 26/00 |
| | | | 606/133 |
| 2014/0305458 A1 | 10/2014 | Brewer et al. | |
| 2018/0092448 A1 * | 4/2018 | Johnson | A45D 29/04 |

* cited by examiner

CALLUS REMOVAL APPARATUS

FIELD OF THE INVENTION

The present invention relates to calluses on hands and feet, and, more particularly, is concerned with an apparatus for removal of calluses, such as from hands and feet.

BACKGROUND OF THE INVENTION

Hyperkeratosis is a thickening and hardening of the outer layer of a person's skin. The outer layer of skin contains a tough, protective protein called keratin. Skin thickening and hardening is a normal response against application of abnormal pressure and friction from rubbing on an area of skin, such as the result of the person's hands and feet being used in the performance of hard work and labor. The abnormal pressure and friction causes the skin to form a hard, protective surface, a callus.

Repeated handling of an object that puts abnormal pressure and/or creates abnormal friction on the hands, such as from tools, sports equipment and the like, typically causes calluses on the hands. Abnormal pressure and friction created by footwear or by walking barefoot causes calluses on the feet.

One conventional process of removing a callus has the following three steps. First, soaking the callused feet/hands with a solution containing baking soda or Epsom salts for half an hour or so to soften the hardened skin. Second, scrubbing the callused feet/hands using a file or pumice stone to remove the calluses. Third, drying the feet/hands and then sprinkling them with a small amount of cornstarch. However, many persons don't have time to follow this lengthy process and so seek to find an alternative approach that can be used equally well to remove calluses in much less time.

Accordingly, there remains a need in the art for an innovation that will overcome the deficiencies of past approaches and the problems that remain unsolved.

SUMMARY OF THE INVENTION

The present invention is directed to an innovation that overcomes the deficiencies of the known art and the problems that remain unsolved by providing an apparatus for removal of calluses, such as from hands and feet. The apparatus is small in size, and can work in all directions and in hard to get at places to remove calluses.

In one aspect of the present invention, a callus removal apparatus includes:
  a main body having opposite first and second end portions and an elongated configuration for ease of gripping with one hand;
  a callus scraping device fitted on the first end portion of the main body, the callus scraping device including
    a head having an exterior face, and
    an array of spaced apart annular edges exposed at the exterior face so as to form a plurality of spaced apart apertures extending through the head and thus capable of contacting, and removing pieces of, a callus by moving the head across and in contact with the callus; and
  a callus sanding device fitted on the second end portion of the main body, the callus sanding device including
    a panel having an exterior face, and
    a plurality of sanding particles attached on the exterior face of the panel and exposed at the exterior thereof and thus capable of contacting, and removing pieces of, a callus by using moving the panel across and in contact with the callus.

In another aspect of the present invention, the spaced apart apertures are aligned in a plurality of rows intersecting at and radiating outward from a central one of the apertures.

In another aspect of the present invention, the main body is hollow, and the first end portion of the main body has an annular end face and an annular ledge on an inside of the first end portion being spaced longitudinally along the first end portion from the annular end face and extending inwardly from the first end portion such that an annular recess is formed on the inside of and about the first end portion and extends longitudinally from the annular end face to the annular ledge. The head of the callus scraping device also has an interior face and an annular peripheral rim portion surrounding the exterior and interior faces and the plurality of spaced apart apertures which extend between the exterior and interior faces of the head. The callus scraping device also includes a connector fixedly attached to the interior face of the head inside of the annular peripheral rim portion of the head, surrounding the plurality of spaced apart apertures, and extending away from the head so as to snugly fit within the first end portion of the main body as at least one of the annular peripheral rim portion of the head makes contact with the annular end face of the main body or the connector at a rear end thereof makes contact with the annular ledge on the inside of the first end portion of the main body. More particularly, the connector may take the form of a plurality of connector legs fixedly attached to the interior face of the head inside of the annular peripheral rim portion of the head, surrounding the plurality of spaced apart apertures, and extending away from the head so as to snugly fit within the first end portion of the main body.

In another aspect of the present invention, the main body is hollow, and the second end portion of the main body has an annular end face and an annular ledge on an outside of the second end portion being spaced longitudinally along the second end portion from the annular end face and extending outwardly from the second end portion such that an annular recess is formed outside of and about the second end portion and extends longitudinally from the annular end face to the annular ledge. The panel of the callus sanding device also has an interior face and an annular peripheral rim portion surrounding the exterior and interior faces and the plurality of sanding particles on the exterior face. The callus sanding device is also joined with a hollow end cap received in the annular recess so as to snugly fit about the outside of the second end portion as at least one of the annular peripheral rim portion of the panel supported at one end of the hollow end cap makes contact with the annular end face of the second end portion of the main body or an opposite end of the hollow end cap makes contact with the annular ledge on the outside of the second end portion of the main body. The main body also has an annular groove formed in the second end portion and about the annular recess and an O-ring seated and compressed in the annular groove when the hollow end cap is snugly fitted along the annular recess about the outside of the second end portion of the main body.

In another aspect of the present invention, a callus removal device includes:
  a hollow main body having opposite first and second end portions and an elongated configuration for ease of gripping the hollow main body with one hand;
  a callus scraping device fitted on the first end portion of the main body, the callus scraping device including a head having a convex-shaped exterior face, and
an array of spaced apart annular edges exposed at the exterior face so as to form a plurality of spaced apart apertures extending through the head and thus capable of contacting, and removing pieces of, a callus by moving the head across and in contact with the callus; and
an end cap fitted on and enclosing the second end portion of the hollow main body and being detachable from the hollow main body to remove callus pieces from the hollow main body.

In another aspect of the present invention, a callus removal device includes:
a hollow main body having opposite first and second end portions and an elongated configuration for ease of gripping the hollow main body with one hand;
a callus scraping device fitted on the first end portion of the hollow main body, the callus scraping device including
a head having a concave-shaped exterior face, and
an array of spaced apart annular edges exposed at the exterior face so as to form a plurality of spaced apart apertures extending through the head and thus capable of contacting, and removing pieces of, a callus by moving the head across and in contact with the callus;
a hollow end cap fitted on and enclosing the second end portion of the hollow main body and being detachable from the hollow main body to remove callus pieces from the hollow main body; and
a callus sanding device fitted on and joined with the hollow end cap, the callus sanding device including
a panel having a planar exterior face, and
a plurality of sanding particles attached on the planar exterior face of the panel and exposed at the exterior of the hollow end cap and thus capable of contacting, and removing pieces of, a callus by moving the panel across and in contact with the callus.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
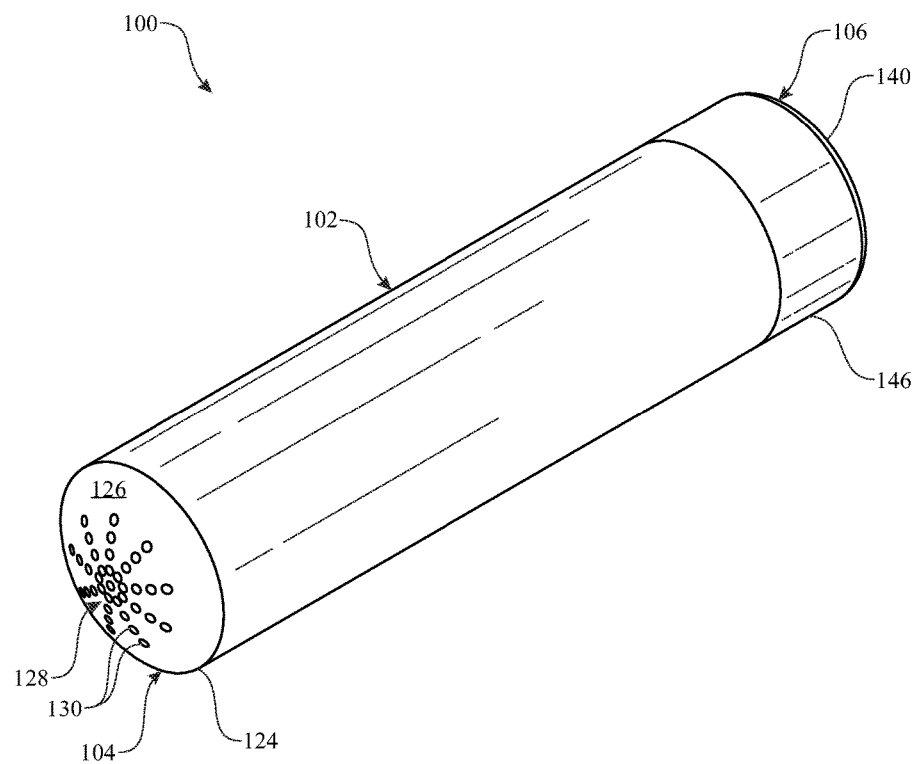
FIG. 1 presents an isometric assembled view of an exemplary embodiment of a callus removal apparatus, being shown from a callus scraping device end of the apparatus.
Figure 2:
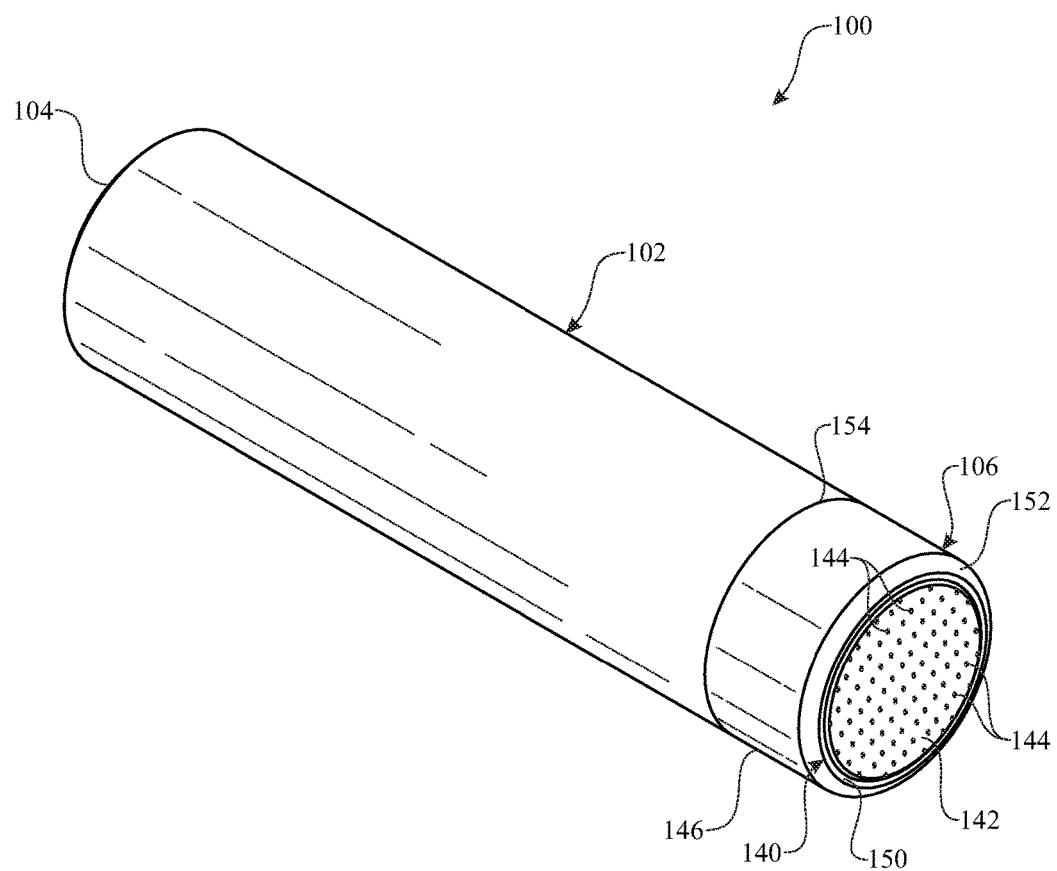
FIG. 2 presents another isometric assembled view of the callus removal apparatus, being shown from a callus sanding device end of the apparatus.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-6, there is illustrated an exemplary embodiment of a callus removal apparatus, generally designated 100, in accordance with aspects of the present invention. The illustrated callus removal apparatus 100 includes a main body 102, a callus scraping device 104, and a callus sanding device 106. The main body 102 has opposite first and second end portions 108, 110. Also, the main body 102 is hollow, made from a suitable plastic or metal, and of an elongated cylindrical shape for ease of gripping with one hand. The callus scraping device 106 is made of a suitable metal and fitted on the first end portion 108 of the main body 102. The callus sanding device 106, in part, is made of a suitable plastic or metal and fitted on the second end portion 110 of the main body 102.

Figure 3:
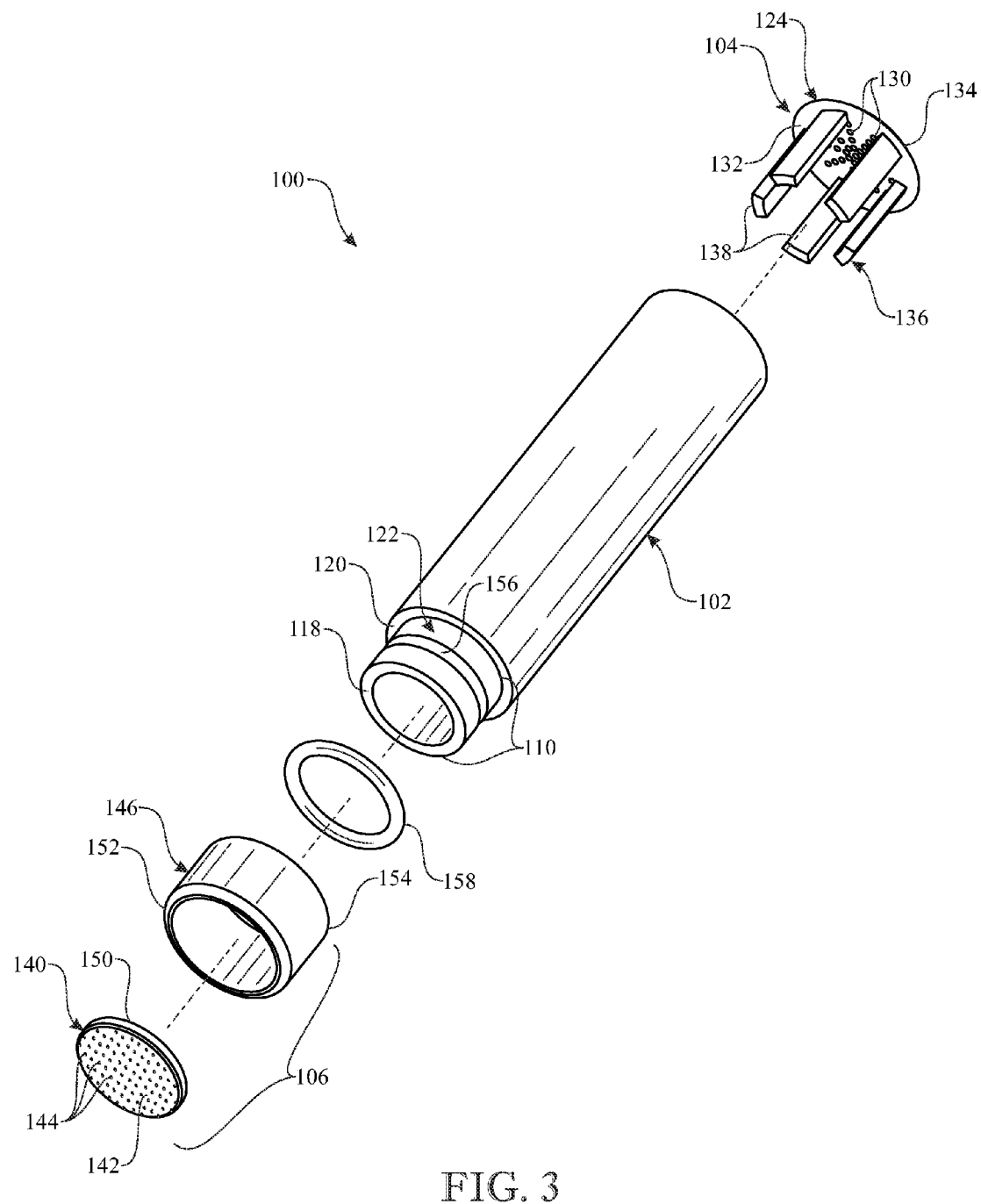
FIG. 3 presents an isometric exploded view of the callus removal apparatus, being shown as originally introduced in FIG. 1.
Figure 4:
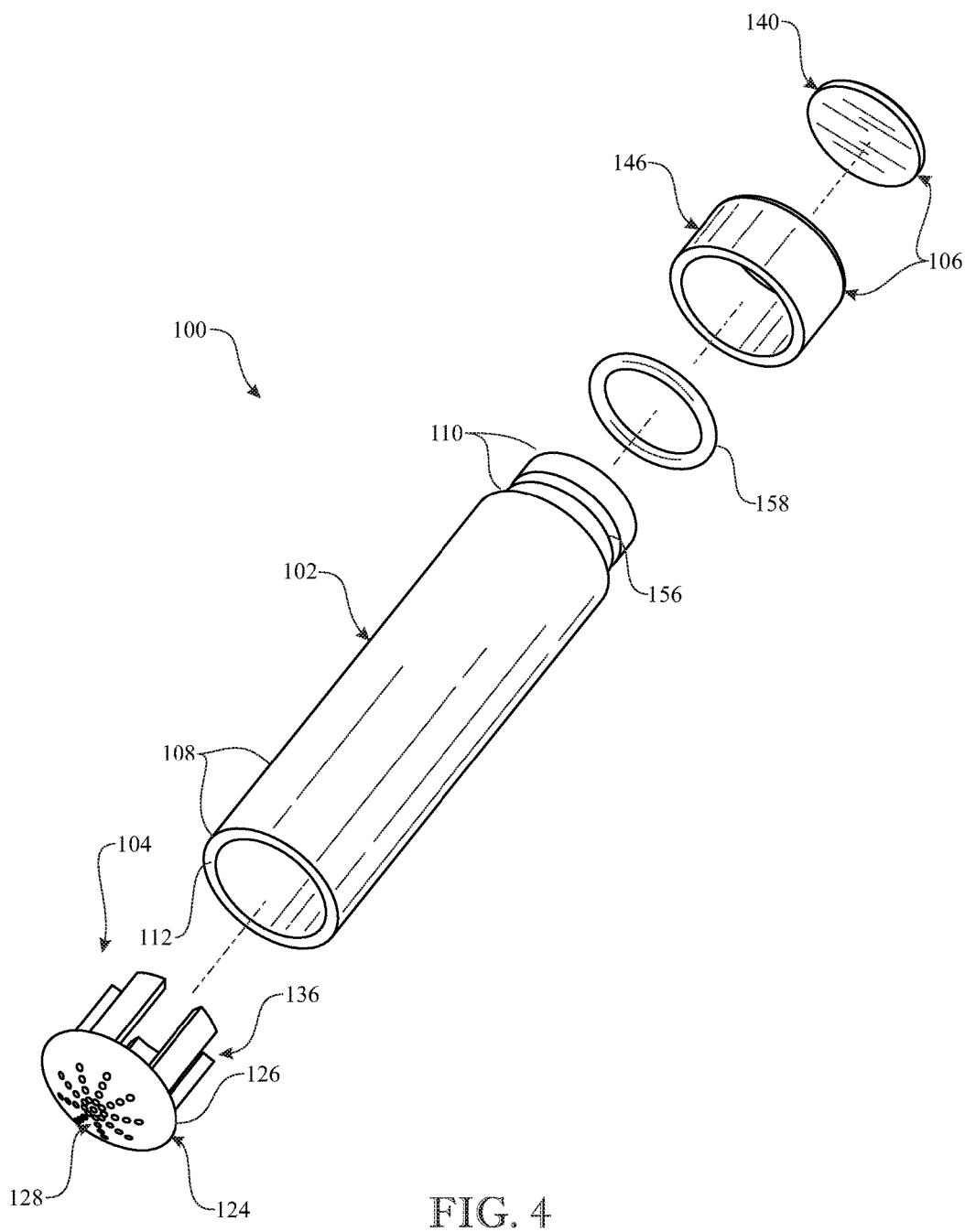
FIG. 4 presents another isometric exploded view of the callus removal apparatus, being shown as originally introduced in FIG. 2.
Figure 5:
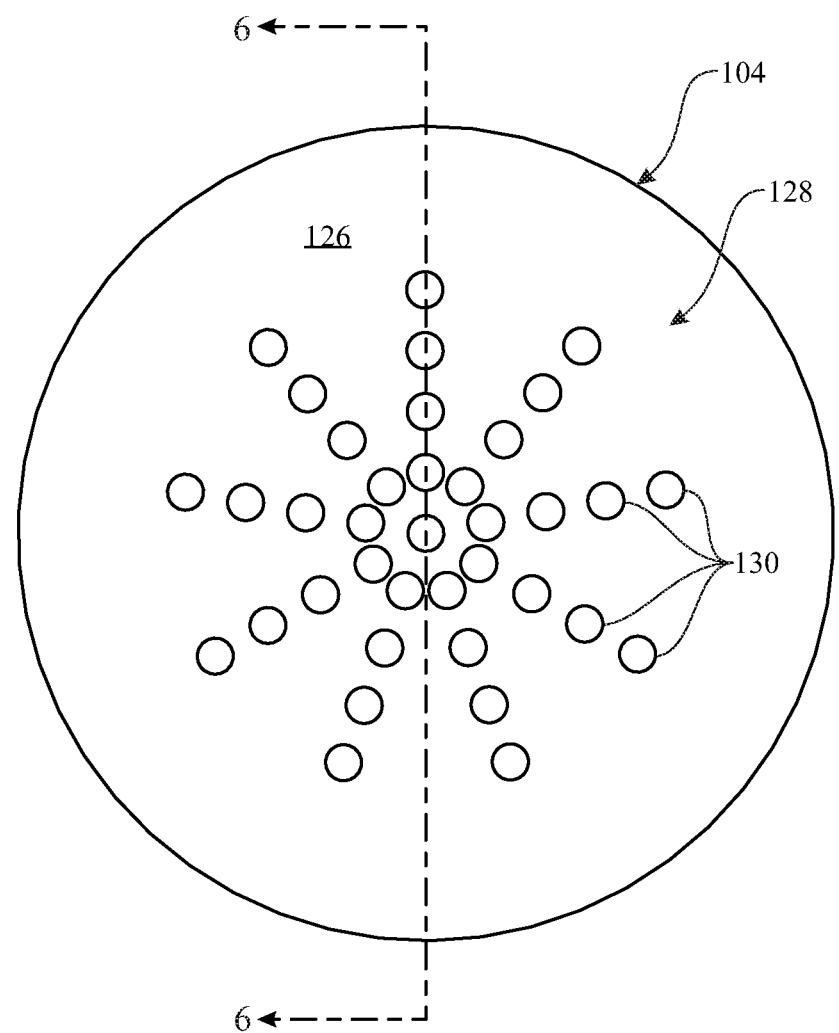
FIG. 5 presents the a front plan view of the callus removal apparatus, being shown from the callus scraping device end of the apparatus.
Figure 6:
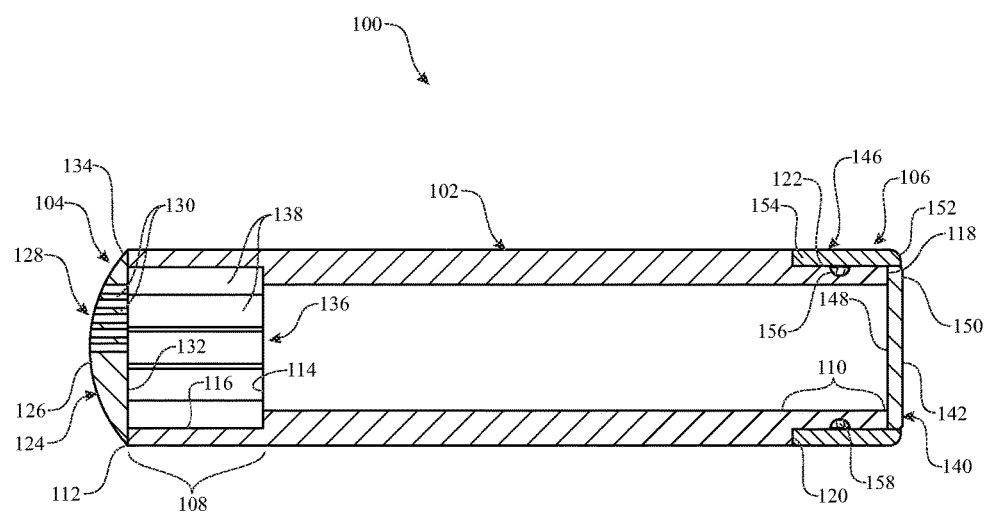
FIG. 6 presents a longitudinal sectional assembled view of the callus removal apparatus taken along section line 6-6 in FIG. 5.

More particularly, as best seen in FIGS. 4 and 6, the first end portion 108 of the main body 102 has an annular end face 112 and an annular ledge 114 on the inside of the first end portion, being spaced longitudinally along the first end portion 108 from the annular end face 112 and extending inwardly from the first end portion such that an annular recess 116 is formed on the inside of and about the first end portion 108 and extends longitudinally from the annular end face 112 to the annular ledge 114. As best seen in FIGS. 3 and 6, the second end portion 110 of the main body 102 has an annular end face 118 and an annular ledge 120 on the outside of the second end portion, being spaced longitudinally along the second end portion 110 from the annular end face 118 and extending outwardly from the second end portion such that an annular recess 122 is formed outside of and about the second end portion 110 and extends longitudinally from the annular end face 118 to the annular ledge 120.

Figure 8:
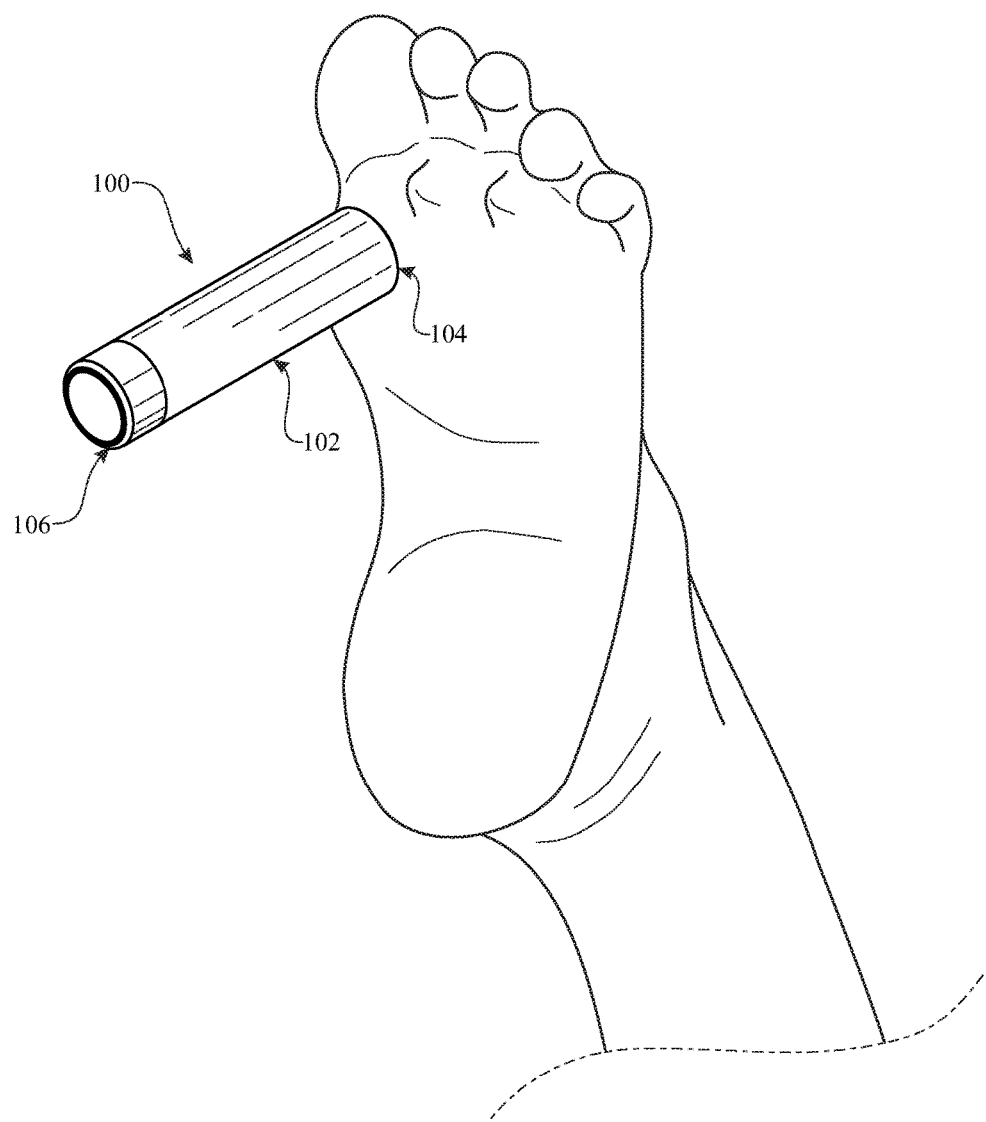
FIG. 8 presents a perspective view of the callus removal apparatus, showing the callus scraping device end of the apparatus being used to remove a callus from a person's foot.

The callus scraping device 104 basically includes a head 124 having an exterior face 126, and an array of spaced apart annular edges 128 exposed at the exterior face that form a plurality of spaced apart apertures 130 extending through the head 124. The exterior face 126 being of convex or dome shape and the spaced apart annular-shaped edges 128 being exposed at the exterior face of the head 124 renders the edges 128 in the exterior face 126 capable of contacting and removing pieces of a callus by gripping the main body 102 with one hand and moving and scraping its head 124, in any direction, across and in contact with a callus, such as shown in FIG. 8. In the one exemplary embodiment seen in FIGS. 1, 4 and 5, the spaced apart apertures 130 are aligned in a plurality of rows intersecting at and radiating outward from a central one of the apertures. Also, the dome-shaped head 124 with the annular edges 128 may be in the form of a cutting screen.

The head 124 of the callus scraping device 104 also has an interior face 132 and an annular peripheral rim portion 134 surrounding the exterior and interior faces 126, 132 and the plurality of spaced apart apertures 130 which extend between the exterior and interior faces of the head. The callus scraping device 104 also includes a connector 136 in the form of a plurality of legs 138 arranged spaced apart from one another in a circular row and fixedly attached to the interior face 132 of the head 124, inwardly of the annular peripheral rim portion 134 of the head and surrounding the plurality of spaced apart apertures 130, so as to extend away from the head. The legs 138 are made of a resilient springy material so that they will yield sufficiently inwardly to snugly fit within the first end portion 108 of the hollow main body 102 as at least one of the annular peripheral rim portion 134 of the head 124 makes contact with the annular end face 112 of the main body 102 or the connector 136 at a rear end thereof makes contact with the annular ledge 114 on the inside of the first end portion 108 of the main body.

Figure 7:
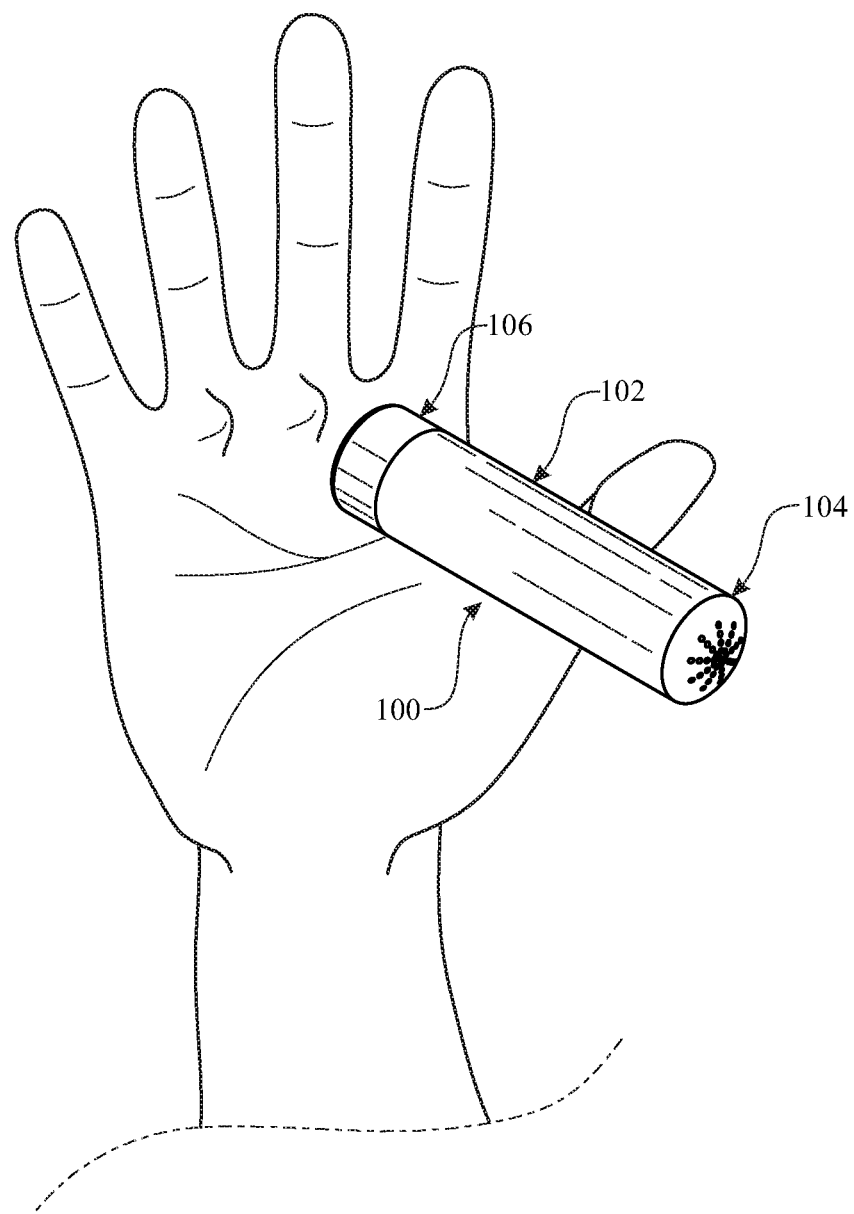
FIG. 7 presents a perspective view of the callus removal apparatus, showing the callus sanding device end of the apparatus being used to remove a callus from a person's hand.

The callus sanding device 106 basically includes a panel 140 having an exterior face 142, and a plurality of sanding particles 144 attached on the exterior face of the panel and exposed at the exterior thereof and thus capable of contacting, and removing pieces of, a callus by gripping the main body 102 with one hand and moving the panel 140 across and in contact with the callus, as shown in FIG. 7. The panel 140 with the sanding particles 144 may be in the form of a piece of 80 GHT sandpaper. Alternatively, the callus removal apparatus 100 may have a hollow end cap 146, with or without the sanding panel 140, fitted on and enclosing the second end portion 110 of the main body 102. The end cap 146 may also be detachable from the second end portion 110 of the main body 102 to remove callus pieces from the hollow main body.

The panel 140 of the callus sanding device 106 also has an interior face 148 and an annular peripheral rim portion 150 surrounding the exterior and interior faces 142, 148 and the plurality of sanding particles 144 on the exterior face. The callus sanding device 106 may also be joined with the hollow end cap 146 received in the annular recess 122 so as to snugly fit about the outside of the second end portion 110 of the main body 102 as at least one of the annular peripheral rim portion 150 of the panel 140 supported at one end 152 of the hollow end cap 146 makes contact with the annular end face 118 of the second end portion 110 of the main body 102 or an opposite end 154 of the hollow end cap 146 makes contact with the annular ledge 120 on the outside of the second end portion 110 of the main body 102. The main body 102 also has an annular groove 156 formed in the second end portion 110 and about the annular recess 122, and an O-ring 158 seated and compressed in the annular groove 156 when the hollow end cap 146 is snugly fitted along the annular recess 122 about the outside of the second end portion of the main body. The presence of the annular groove 156 and O-ring 158 enables ease of removal and replacement of the end cap 146 from and back on the second end portion 110 of the main body 102 of the callus removal apparatus 100.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A callus removal apparatus, comprising:
    a main body having an elongated configuration for ease of gripping with one hand, said main body comprising:
        opposite first and second end portions where a longitudinal axis extends between said first and second end portions, and
        an opening disposed at said first end portion and extending transversely to the longitudinal axis, said opening being in fluid communication with a hollow interior of the main body;
    a callus scraping device fitted on said first end portion of said main body, said callus scraping device comprising:
        a head extending over said opening, said head having an exterior face of convex or concave shape, and
        an array of spaced apart annular edges exposed at said exterior face so as to form a plurality of spaced apart apertures extending through said head and thus capable of contacting and removing pieces of a callus by moving said head across and in contact with the callus; and
    a callus sanding device fitted on said second end portion of said main body, said callus sanding device comprising:
        a panel having an exterior face where said panel extends transversely with respect to the longitudinal axis, and
        a plurality of sanding particles attached on said exterior face of said panel and exposed at the exterior thereof and thus capable of contacting and removing pieces of a callus by moving the panel across and in contact with the callus,
    wherein at least one of said callus scraping device and said callus sanding device are removably fitted to said main body providing access to said hollow interior such that during use, pieces of callus collected within the hollow interior may be discarded by removal of said at least one of said callus scraping device and said callus sanding device.

2. The apparatus as recited in claim 1 wherein said spaced apart apertures are aligned in a plurality of rows intersecting at and radiating outward from a central one of said apertures.

3. The apparatus as recited in claim 1 wherein
said first end portion of said main body has an annular end face and an annular ledge on an inside of said first end portion being spaced longitudinally along said first end portion from said annular end face and extending inwardly from said first end portion such that an annular recess is formed on the inside of and about said first end portion and extends longitudinally from said annular end face to said annular ledge.

4. The apparatus as recited in claim 3 wherein said head of said callus scraping device also has an interior face and an annular peripheral rim portion surrounding said exterior and interior faces and said plurality of spaced apart apertures which extend between said exterior and interior faces of said head.

5. The apparatus as recited in claim 4 wherein said callus scraping device also comprises a connector fixedly attached to said interior face of said head inside of said annular peripheral rim portion of said head, surrounding said plurality of spaced apart apertures, and extending away from said head so as to snugly fit within said first end portion of said main body as at least one of said annular peripheral rim portion of said head makes contact with said annular end face of said main body or said connector at a rear end thereof makes contact with said annular ledge on the inside of said first end portion of said main body.

6. The apparatus as recited in claim 1 wherein
said callus sanding device is also joined with an end cap at one end fitted on said second end portion of said main body and detachable from said main body to remove callus pieces from said main body, said end cap at an opposite end supporting said panel.

7. The apparatus as recited in claim 1 wherein
said second end portion of said main body has an annular end face and an annular ledge on an outside of said second end portion being spaced longitudinally along said second end portion from said annular end face and extending outwardly from said second end portion such that an annular recess is formed outside of and about said second end portion and extends longitudinally from said annular end face to said annular ledge.

8. The apparatus as recited in claim 7 wherein:
said panel of said callus sanding device also has an interior face and an annular peripheral rim portion surrounding said exterior and interior faces and said plurality of sanding particles on said exterior face; and
said callus sanding device is also joined with a hollow end cap received in said annular recess so as to snugly fit about the outside of said second end portion as at least one of said annular peripheral rim portion of said panel supported at one end of said hollow end cap makes contact with said annular end face of said second end portion of said main body or an opposite end of said hollow end cap makes contact with said annular ledge on the outside of said second end portion of said main body.

9. The apparatus as recited in claim 8 wherein said main body has an annular groove formed in said second end portion and about said annular recess, and an O-ring seated and compressed in said annular groove when said hollow end cap is snugly fitted along said annular recess about the outside of said second end portion of said main body.

10. The apparatus as recited in claim 1 wherein said callus scraping device also comprises a plurality of connector legs fixedly attached to said interior face of said head inside of said annular peripheral rim portion of said head, surrounding said plurality of spaced apart apertures, and extending away from said head so as to snugly fit within said first end portion of said main body as at least one of said annular peripheral rim portion of said head makes contact with said annular end face of said main body or said connector legs at rear ends thereof make contact with said annular ledge on the inside of said first end portion of said main body.

11. A callus removal apparatus, comprising:
a hollow main body having an elongated configuration for ease of gripping said hollow main body with one hand, said hollow main body comprising:
opposite site first and second end portions where a longitudinal axis extends between said first and second end portions and
an opening disposed at sad first end portion and extending transversely to the longitudinal, said opening being in fluid communication with a hollow interior of the main body;
a callus scraping device fitted on said first end portion of said hollow main body, said callus scraping device comprising:
a head extending over said opening, said head having a concave-shaped exterior face, and
an array of spaced apart annular edges exposed at said exterior face so as to form a plurality of spaced apart apertures extending through said head and thus capable of contacting, and removing pieces of, a callus by moving said head across and in contact with the callus;
a hollow end cap fitted on and enclosing said second end portion of said hollow main body and being detachable from said hollow main body such that during use, pieces of callus collected within the hollow interior may be discarded by removal of said hollow end cap from sad hollow main body; and
a callus sanding device fitted on and joined with said hollow end cap, said callus sanding device comprising:
a panel having a planar exterior face where sad panel extends transversely with respect to the longitudinal axis, and
a plurality of sanding particles attached on said planar exterior face of said panel and exposed at the exterior thereof and thus capable of contacting, and removing pieces of, a callus by moving sad panel across and in contact with the callus.

12. The apparatus as recited in claim 11 wherein said hollow main body also has an annular groove formed in and about said second end portion, and an O-ring seated and compressed in said annular groove when said hollow end cap is snugly fitted about the outside of said second end portion of said main body.

13. The apparatus as recited in claim 11 wherein said spaced apart apertures are aligned in a plurality of rows intersecting at and radiating outward from a central one of said apertures.

\* \* \* \* \*